United States Patent [19]

Raab

[11] 4,280,233

[45] Jul. 28, 1981

[54] BONE CONNECTIVE PROSTHESIS COMPRISING A REINFORCEMENT ELEMENT CARRYING A POLYMER LAYER HAVING A VARYING MODULUS OF ELASTICITY

[76] Inventor: Simon Raab, 5872 Westbury Ave., Montreal, Quebec, Canada, H3W 2W9

[21] Appl. No.: 63,434

[22] Filed: Aug. 3, 1979

[30] Foreign Application Priority Data

Feb. 15, 1979 [GB] United Kingdom ............... 05445/79

[51] Int. Cl.³ ................................................ A61F 1/24
[52] U.S. Cl. ......................................... 3/1.91; 3/1.911;
3/1.913; 128/92 C; 428/170; 428/218; 428/305
[58] Field of Search ............. 128/92 C, 92 CA; 3/1.9,
3/1.91, 1.911, 1.912, 1.913; 428/463, 520, 170,
218, 305; 156/232; 427/2

[56] References Cited

U.S. PATENT DOCUMENTS

| | | | |
|---|---|---|---|
| 3,623,164 | 11/1971 | Bokros ........................................ | 3/1 |
| 3,707,006 | 12/1972 | Bokros et al. ....................... | 128/92 C |
| 3,781,917 | 1/1974 | Mathys ........................... | 128/92 CA |
| 3,806,960 | 4/1974 | Weber ................................ | 128/92 C |
| 3,879,767 | 4/1975 | Stubstad ............................ | 128/92 C |
| 3,893,196 | 7/1975 | Hochman ............................... | 3/1.913 |
| 3,938,198 | 2/1976 | Kahn et al. ............................ | 3/1.912 |
| 3,986,212 | 10/1976 | Sauer ..................................... | 3/1.91 |

FOREIGN PATENT DOCUMENTS 2309432 11/1973 Fed. Rep. of Germany ............ 3/1.91
2253338 5/1974 Fed. Rep. of Germany ............. 3/1.9

OTHER PUBLICATIONS

Jastrzebski, Zbignieu, *The Nature and Properties of Engineering Materials,* John Wiley and Sons, 1976, p. 410.

*Primary Examiner*—William F. Smith
*Assistant Examiner*—Chris Konkol
*Attorney, Agent, or Firm*—Roylance, Abrams, Berdo & Farley

[57] ABSTRACT

Improved bone connective prostheses are disclosed. The prostheses comprise a reinforcement element carrying a polymer layer having a varying modulus of elasticity. The exterior surface of the polymer layer constitutes the bone attachment surface of the prostheses and has the lowest modulus of elasticity. The interior surface of the polymer layer is attached to reinforcement element and has the highest modulus of elasticity. Portions of the polymer layer lying between the exterior and the interior surface of the polymer layer have moduli of elasticity which are intermediate with respect to the moduli of elasticity of the exterior and interior surface of the layer. The modulus of elasticity of the layer decreases in the direction of interior to exterior. The decrease in modulus of elasticity may be either continuous or incremental. The reinforcement element may have either a simple or a complex structure.

21 Claims, 8 Drawing Figures

BONE CONNECTIVE PROSTHESIS COMPRISING A REINFORCEMENT ELEMENT CARRYING A POLYMER LAYER HAVING A VARYING MODULUS OF ELASTICITY

BACKGROUND OF THE INVENTION

1. Field of the Invention

The present invention relates to prostheses adapted to be fixedly attached to bone by means of bone cement. Specifically, the present invention is directed to prostheses adapted to maximize the durability of the prosthesis-bone cement adherence.

2. Description of the Prior Art

In the field of orthopedic surgery, metal alloys such as ZIMALOY manufactured by Zimmer U.S.A., Inc., a chromium-cobalt-molybdenum alloy, stainless steel and titanium alloys, and highly rigid plastics such as ultra-high molecular weight polyethylene (hereinafter UHMWPE) have been used successfully to replace the ends of long bones and joints including the hip joint. However, there exists a severe limitation with respect to this type of orthopedic surgery, namely, coupling of the prostheses to bone. Due to such factors as mechanical stress, fatigue, corrosion, etc., the prostheses-bone cement joints have been prone to failure. As disclosed in applicant's co-pending patent application, Ser. No. 45,657, filed June 5, 1979; entitled "Bone Connective Prostheses Adapted to Maximize Strength and Durability of Prosthese-Bone Cement Interface; and Methods of Forming Same", improved bone-connective prostheses may be prepared by treating a rigid prosthetic element, adapted to be joined to bone by means of bone cement, to provide an adherent polymethylmethacrylate film on the surface thereof. Prosthetic elements bearing a polymethylmethacrylate film as disclosed in applicant's co-pending application can more readily be joined to bone cement and provide a stronger and more durable joint.

However, an additional problem with respect to bone connective prostheses relates to the differences between the rigidity of the prosthetic element and the bone cement. Thus, prosthetic elements designed to be attached to bone, e.g., stem insert prostheses and bone resurfacing prostheses, are generally composed of a very rigid material such as a metal alloy or UHMWPE. On the other hand, bone cement, which normally comprises a mixture of polymethylmethacrylate and methyl methacrylate monomer and which may additionally include a styrene copolymer of methyl methacrylate, is typically a less rigid, porous material. Accordingly, when such a rigid prosthetic element is joined to bone by means of bone cement and the resultant composite subjected to force, e.g., walking in the case of a hip ball joint implant, the interface between the rigid implant and the less rigid bone cement is subjected to a high degree of mechanical stress. Moreover, extreme non-physiological force distribution (in the bone) can occur as well as extreme stress concentration in the prosthesis-cement complex, resulting in bone atrophy, weakening of the bone, loss of interfacial integrity and subsequent fracture of one or more of the components. Additionally, these forces can result in a fatigue or brittle fracture of the bone cement since the cement typically includes flaws such as voids, thus leading to failure of the prosthesis.

SUMMARY OF THE INVENTION

It has now been discovered that prostheses fixation problems may be overcome by the utilization of the improved prostheses of the present invention wherein the surface of the prosthetic element, which is designed to be attached to bone, consists of a polymer layer having substantial thickness and being disposed upon a reinforcement element. The polymer layer is designed so as to have a varying modulus of elasticity such that the exterior surface, which is designed to be attached to bone, is less rigid, i.e., has a lower modulus of elasticity, and the interior surface of the polymer layer which is attached to the reinforcement element is more rigid, i.e., has a greater modulus of elasticity. The portions of the layer which lie between the exterior and interior surface of the polymer layer have moduli of elasticity which are intermediate with respect to the moduli of elasticity of the exterior and interior surfaces of the polymer layer. Additionally, the modulus of elasticity varies throughout the layer such that the modulus of elasticity decreases in the direction of interior to exterior. Preferably, the modulus of elasticity of the exterior surface of the polymer layer is designed so that it is approximately equal to the modulus of elasticity of bone cement while the modulus of elasticity of the interior surface of the polymer layer is designed so that it is approximately equal to the modulus of elasticity of the reinforcement element. Thus, a more even force distribution can occur as the force is distributed throughout the polymer layer rather than being concentrated at the interface between a rigid prosthesis and a less rigid bone cement.

According to one aspect of the present invention, the modulus of elasticity is continuously varied throughout the polymer layer. This may be accomplished by the provision of a polymer layer containing voids wherein the voids are distributed throughout the layer such that the percentage of volume occupied by voids in portions of the layer adjacent its exterior surface is greater than the percentage of volume occupied by voids in portions of the layer adjacent the interior surface, and wherein the void volume percentage continuously increases from the interior of the layer to the exterior of the layer.

According to another aspect of the present invention, the polymer layer having a varying modulus of elasticity may be provided such that the modulus of elasticity varies incrementally. This may be accomplished by providing a polymer layer which is composed of several discrete layers, and wherein each layer has a different modulus of elasticity. Thus, each layer may contain varying amounts of plasticizer to provide layers having different moduli of elasticity. Alternatively, the different layers may contain varying amounts of reinforcement fillers such as fibers (wound or dispersed), or particulate fillers such as glass beads, etc. The modulus of elasticity of each layer may also be varied by varying the chemical and physical constituency of the different layers.

According to another aspect of the present invention, the reinforcement element carrying the polymer layer may be designed so that it has a more complex shape than the exterior of the polymer layer. Thus, in the case of prior art stem insertion prostheses, the stem was required to have a frustoconical shape with a regular surface in order that it could be inserted into the interior of the bone cement. By utilization of the present invention, a reinforcement element may be designed so that it has a complex shape designed to give even distribution of forces and be covered with a polymer layer such that the composite stem insertion prosthesis comprising the reinforcement element and the polymer layer has a single frustoconical shape with a smooth surface.

BRIEF DESCRIPTION OF THE DRAWINGS

In the drawings which form a part of the original disclosure of the present invention.

DETAILED DESCRIPTION OF THE INVENTION

According to the present invention, prostheses designed to be fixedly attached to bone by means of bone cement are provided whereby the force distribution between the bone, bone cement and prosthesis may be more evenly and properly distributed than in prior art prostheses. Such prostheses comprise a reinforcement element, which is composed of a rigid material such as a chromium-cobalt-molybdenum alloy, e.g., ZIMALOY, or a titanium or stainless steel alloy or a polymer such as UHMWPE, with at least a portion of the surface of the reinforcement element carrying a polymer layer having substantial thickness. The exterior surface of the polymer layer constitutes the bone attachment surface of the prosthesis. The interior surface of the polymer layer is secured to the reinforcement element. The polymer layer is designed so as to have a varying modulus of elasticity such that the modulus of elasticity in portions of the layer adjacent the interior surface of the layer is essentially constant and the modulus of elasticity of portions of the layer adjacent the exterior surface of the layer is likewise essentially constant. The modulus of elasticity of the portions of the layer adjacent the interior surface is greater than the modulus of elasticity of the portions of the layer adjacent the exterior surface while the modulus of elasticity of portions of the layer lying between the exterior and the interior portions decreases in the direction of interior to exterior. Preferably, the modulus of elasticity of the exterior surface of the layer is approximately equal to the modulus of elasticity of hardened bone cement. It is also preferred that the modulus of elasticity of the interior portion of the layer be approximately equal to the modulus of elasticity of the reinforcement element.

Figure 1:
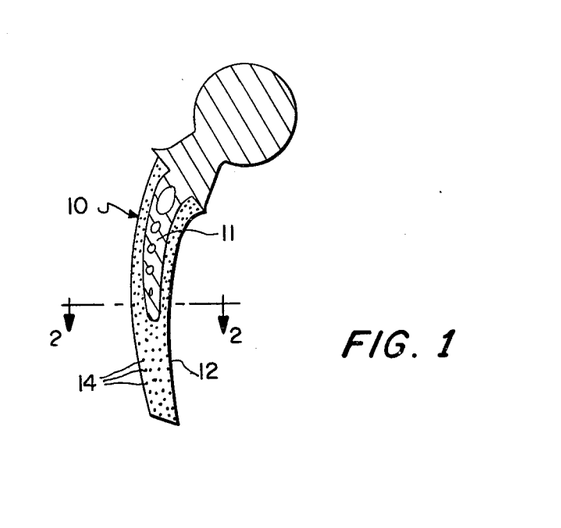
FIG. 1 is a side elevational view in longitudinal section of a hip prosthesis designed in accordance with the present invention wherein a reinforcement element is covered by a polymer layer which is constructed such that the rigidity of the layer is greater at the interior than at the exterior.
Figure 2:
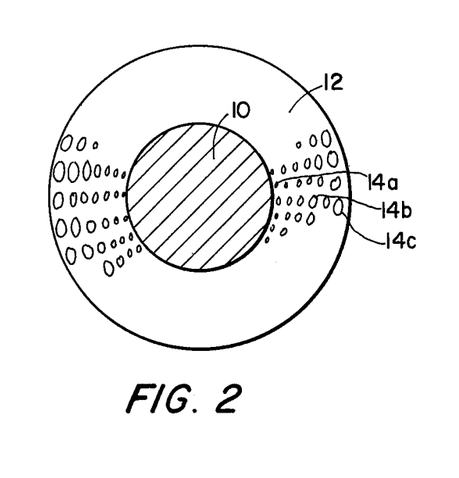
FIG. 2 is an enlarged top plan view in section taken along lines 2—2 in FIG. 1 and illustrates the varying porosity of the polymer layer shown in FIG. 1.
Figure 3:
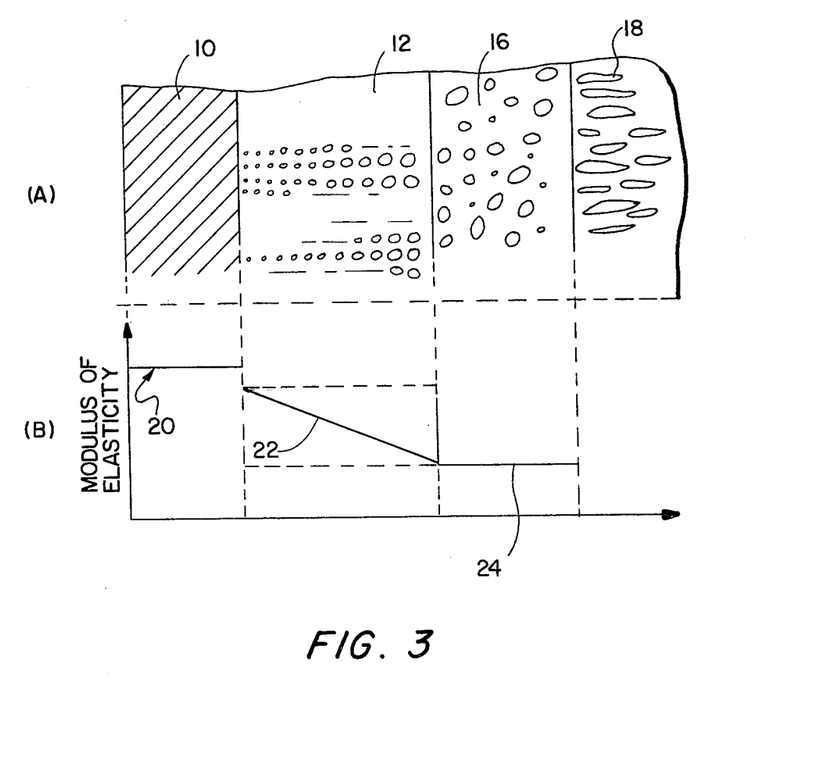
FIG. 3 diagrammatically illustrates a fragmentary cross-section of an encapsulated implant as in FIGS. 1 and 2 which has been fixedly attached to bone by means of bone cement, beneath which there is shown a graph of the elastic moduli of the different components of the reinforcement element/polymer layer/bone-cement/bone composite.

The polymer layer having a varying modulus of elasticity may be a single continuous layer or it may be composed of several discrete polymer layers, each having a different modulus of elasticity. A prosthesis having a single, continuous polymer layer disposed upon a reinforcing element is shown in FIGS. 1, 2 and 3. FIG. 1 is an elevational side view in longitudinal section of a stem insertion hip prosthesis 10 comprising a reinforcement element 11 carrying a high strength polymer layer 12 which has substantial thickness and which is preferably composed of polymethylmethacrylate. This layer includes voids 14 within the interior thereof.

In FIG. 2 there is illustrated a top plan view of a cross-section of the bone implant prosthesis of FIG. 1 taken at line 2—2. The implant reinforcement element 10 is a rigid material such as a metal alloy or UHMWPE. The polymer layer 12 is shown to include voids 14a, 14b and 14c. The voids nearer the interior of the polymer layer represented by 14a are shown to be smaller than the voids located at the exterior of the polymer layer represented by void 14c. Void 14b, which lies linearly between voids 14a and 14c, is shown to be of an intermediate size. Accordingly, it will be seen that the rigidity of the polymer layer is continuously varied from a high rigidity at the interior of the polymer capsule where the degree of porosity approaches zero, to a low rigidity at the exterior of the polymer capsule where the degree of porosity is much greater. In fact, rigidity of the polymer capsule is controlled not only by the size of the individual voids but also by the number of individual voids in a given portion of the capsule. Thus, when the percentage of volume occupied by voids in a given portion of the capsule is great, that portion of the layer will be relatively flexible, i.e., will have a low modulus of elasticity. On the other hand, when the void volume percentage is low or near zero in a portion of the layer, such portion of the polymer layer will be highly rigid, i.e., have a high modulus of elasticity.

In FIG. 3, there is a shown a diagrammatic fragmentary cross-section of an implant as in FIGS. 1 and 2 which has been fixedly attached to bone by means of bone cement. Also shown in the lower portion of FIG. 3 is a graph of the elastic moduli of the different components of the reinforcement element/polymer layer/bone cement/bone composite. Thus, reinforcement element 10 is shown to have a relatively high elastic modulus represented by the straight line 20. The polymer layer 12 having a continuously varying porosity is shown to have a continuously varying modulus of elasticity represented by line 22 in the graph. At the interior of the polymer layer where the porosity closely approaches zero, it can be seen that the modulus of elasticity of the polymer layer is nearly that of the reinforcement element. At the exterior of the polymer layer where the voids volume percentage is much greater, it can be seen that the elastic modulus is of a much lower value, preferably closely approximating the modulus of elasticity of hardened bone cement. Hardened bone cement 16 is shown lying between the polymer layer 12 and bone 18. The modulus of elasticity of the hardened bone cement is shown to have a constant value as indicated by line 24. Thus, ideally, the rigidity of the polymer layer 12 is varied so that at the interior of the layer, its modulus of elasticity is approximately equal to the modulus of elasticity of the implant reinforcement element while at the exterior of the layer, which constitutes the bone attachment surface of the prosthesis, its modulus of elasticity is approximately equal to the modulus of elasticity of the bone cement which is low due to the nature of bone cement itself and due to the presence of voids and flaws in bone cement.

As indicated previously, the polymer layer has substantial thickness. By the term "substantial thickness", it is meant that the polymer layer is sufficiently thick that the modulus of elasticity of the layer may be varied either continuously or incrementally as hereinbefore and hereinafter described. Polymer layers which can be utilized in the present invention should have a minimum thickness of about 0.1 cm., preferably about 0.5 cm., most preferably about 0.5–1.0 cm.

Formation of the prostheses illustrated in FIGS. 1, 2 and 3 wherein a single polymer layer containing voids is disposed upon a reinforcement element, and wherein the modulus of elasticity of the polymer layer is varied from interior to exterior by variation of the percentage of volume occupied by the voids from interior to exterior may be accomplished by any suitable means. One method which may be utilized is to vary the rate of solidification of the polymer layer linearly from the exterior to the interior or from the interior to the exterior, while at the same time varying the degree of porosity within the non-solid polymer.

Thus, the polymer capsule may be formed from a molten PMMA thermoplastic and the rate of solidification of the thermoplastic may be controlled by controlling the temperature of the thermoplastic. The molten thermoplastic is confined in a closed mold having the desired shape for the bone implant. The reinforcement portion or stem of the implant, comprising a metal alloy will also be enclosed in the mold at the center thereof. A portion of the metal alloy comprising a non-reinforcing portion of the implant is not enclosed in the mold. The metal alloy exhibits a high degree of heat conductivity and may be contacted with a cooling means such as a forced supply of cool air, a liquid nitrogen stream, etc. Utilizing this arrangement, the polymer at the interior of the mold, which is in contact with the cool reinforcement stem will harden first while the polymer at the exterior of the mold will be cooled at a later point and thus will solidify at a later point.

The molten polymer within the mold has an inert gas such as, for instance, nitrogen or carbon dioxide dissolved therein. The amount of gas dissolved in the polymer is controlled such that at high pressures all of the gas is dissolved in the liquid polymer while at lower pressures the gas will exist as discrete bubbles or voids. The mold is designed so that pressure within the mold may be continuously varied. Accordingly, utilizing such an arrangement, the pressure within the mold is continuously varied from a higher value wherein all the gas is dissolved in the polymer to a lower value wherein only a small percentage of the gas is dissolved in the polymer. At the same time a cooling means is applied to the heat conductive reinforcing stem in the center of the mold. Therefore, when the polymer in the interior of the mold hardens, it will contain no voids since at that time the pressure in the mold is such that all of the gas is dissolved in the polymer. However, when the polymer at the exterior of the mold hardens it will contain voids since the pressure in the mold is, at that time, at a value such that the gas in the polymer exists in the gaseous phase.

Another method of forming the varying porosity polymer layer of the present invention may be utilized when it is desired to form the polymer layer from a polymerizable material such as a crosslinkable PMMA polymer, a monomer, or a polymer-monomer admixture containing a heat sensitive polymer catalyst or initiator. In such a case, a gas is again dissolved in the polymerizable material and a closed mold is likewise utilized. However, the implant reinforcement element should be heated and thus the heated material at the interior of the mold will polymerize first. As with the above example, if the pressure at the interior of the mold is continuously decreased as a function of the rate of polymerization, the material at the interior of the mold will contain no voids while the material at the exterior of the mold will contain a high degree of voids.

In the foregoing discussions, reference has been made to dissolving gases in polymers and polymerizable liquids in order to promote void formation. However, in the case of some polymerizable liquids, such as a mixture of methyl methacrylate monomer and PMMA, porosity is inherently produced when such mixtures are allowed to polymerize in the absence of pressure. When such a polymerizable mixture is used, no special gas dissolving step will be required.

Still another method which may be utilized to form the polymer layer having a varying porosity involves the use of a temperature sensitive foaming agent. Thus, a non-heat sensitive polymerizable material containing a heat sensitive blowing agent may be enclosed in the mold under conditions such that polymerization is initiated by, e.g., inclusion of an ambient temperature polymerization catalyst. Heat is applied to the exterior portion of the mold so that the polymer thereat containing the heat sensitive foaming agent will include voids while the relatively cooler material at the interior of the mold will contain no voids. The heat sensitive foaming agent and the gas produced thereby should be non-physiologically active in order that the polymer layer not interact negatively with bone.

Finally, the process of post expansion may be utilized to form the polymer layer having varying porosity. Thus, a layer of thermoplastic material comprising a dissolved foaming agent such as pentane or nitrogen is molded to the exterior of the reinforcing element and allowed to harden. The exterior of the hardened layer is exposed to a heat means such as an infrared radiation source, thus warming and softening the exterior portion of the thermoplastic layer. At this point, the dissolved foaming agent reverts to a gaseous phase producing voids in the polymer layer. Upon completion of sufficient foaming, the heat source is removed and the layer allowed to harden.

As previously indicated, the polymer layer having a varying modulus of elasticity may comprise several discrete layers rather than a single continuous layer. In such a case, the most exterior discrete layer of the composite polymer layer will have a low modulus of elasticity and thus be relatively flexible. Preferably, this discrete layer which comprises the bone attachment surface will have a modulus of elasticity which is approximately equal to that of hardened bone cement. The most interior discrete layer of the composite polymer layer which comprises the layer directly secured to the reinforcement element, will have a high modulus of elasticity and thus be relatively rigid. It is preferred that modulus of elasticity of this most interior discrete layer be approximately equal to the modulus of elasticity of the reinforcement element. The intervening polymer layers have moduli of elasticity intermediate of the moduli of the exterior and interior layers such that each layer has a smaller modulus than that of the adjacent, more interior layer.

Figure 4:
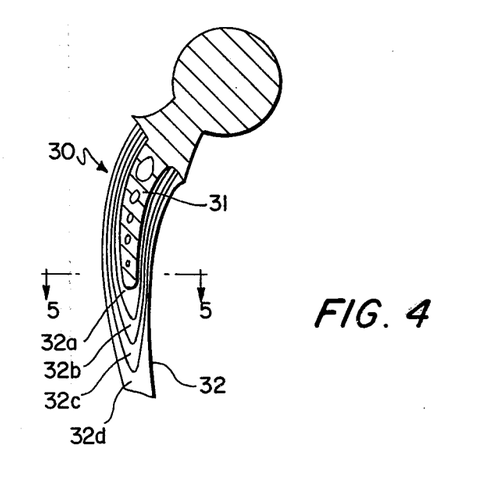
FIG. 4 is a side elevational view in longitudinal section of a polymer encapsulated hip prosthesis wherein the polymer layer is a composite of several discrete polymer layers and wherein the modulus of elasticity of each of the discrete polymer layers is different.
Figure 5:
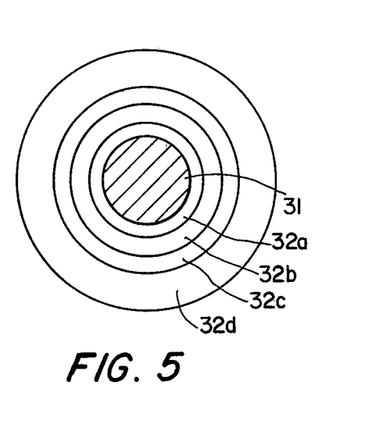
FIG. 5 is an enlarged top plan view in section taken along lines 5—5 in FIG. 4 illustrating the multi-layered polymer layer shown in FIG. 4.
Figure 6:
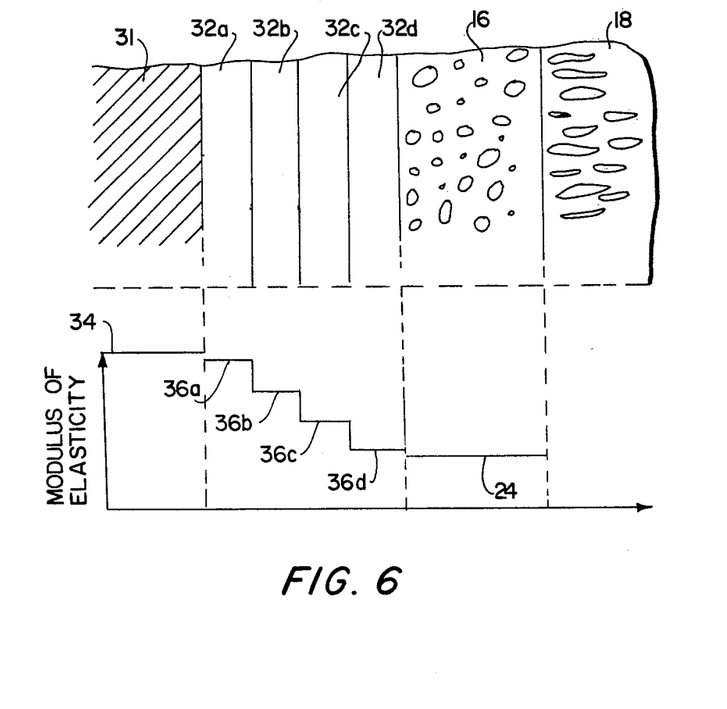
FIG. 6 diagrammatically illustrates a fragmentary cross-section of an encapsulated implant as in FIGS. 5 and 6, which has been fixedly attached to bone by means of bone cement, beneath which there is shown a graph of the elastic moduli of the different components of the reinforcement element/discrete polymer layers/bone cement/bone composite.

A prosthesis comprising a reinforcement element carrying a polymer layer having a varying modulus of elasticity wherein the polymer layer is a composite of discrete polymer layers is illustrated in FIGS. 4, 5 and 6. FIG. 4 is an elevational side view in longitudinal section of a stem insertion hip joint prosthesis wherein the reinforcement element carries a composite polymer layer comprising four discrete polymer layers. Thus, in FIG. 4 there is shown a stem insertion prosthesis 30 comprising a rigid reinforcement element 31 carrying a multi-layered composite polymer layer 32. The polymer layer is composed of four layers 32a, 32b, 32c and 32d, each of which has a different modulus of elasticity.

FIG. 5 is an enlarged top plan view in section taken along lines 5—5 in FIG. 4 and illustrates the different layers of the polymer layer 32 shown in FIG. 4. The reinforcement element 31 comprises a metal alloy or UHMWPE which has a high modulus of elasticity. The most interior polymer layer 32a is constructed to have a high modulus of elasticity, preferably closely approximating that of the reinforcement element. The most exterior polymer layer 32d has the lowest modulus of elasticity, preferably approximating that of hardened bone cement. The two polymer layers 32b and 32c are shown lying between the interior and exterior polymer layers 32a and 32d, respectively. Polymer layer 32c has a modulus of elasticity which is lesser than that of layer 32b while being greater than that of polymer layer 32d. Polymer layer 32b has a modulus of elasticity which is lesser than that of polymer layer 32a while being greater than that of polymer layer 32c.

The modulus of elasticity of the different discrete polymer layers can be varied by varying the amount of plasticizer included in each layer. Thus, for example, polymer layer 32a may be composed of polymethylmethacrylate with no plasticizer. Polymer layer 32b may be composed of polymethylmethacrylate including a small amount of plasticizer. Polymer layer 32c may be composed of polymethylmethacrylate having a greater amount of plasticizer than that included in layer 32b. Polymer layer 32d may be composed of polymethylmethacrylate having an even greater amount of plasticizer than the amount included in layer 32c.

In a like manner, the modulus of elasticity of each layer can be varied by including varying amounts of reinforcement fillers, either fiberous or particulate, in each layer. Generally, the inclusion of reinforcement fillers, either fiberous or particulate, in polymer compositions will increase the elastic modulus or stiffness of the composition. The degree of increase, however, is dependent on numerous factors including the polymer composition utilized, the chemical make-up of the filler and the physical characteristics of the filler such as size, shape and density in the case of particulate fillers or, in the case of fiberous fillers, the length, diameter and stiffness of the particular fiber. Further information regarding the inclusion of reinforcement fillers in polymers and the effect on stiffness or elastic modulus may be found in "Reinforced Thermoplastics" by W. V. Titow and B. J. Lanham; Halsted Press, a Division of John Wiley & Sons, Inc. (New York, 1975), especially pages 9–16 and 111–116 and references cited therein. The disclosure of these pages is hereby incorporated by reference.

Fiberous reinforcements, either wound or dispersed, which may by utilized include glass fibers, carbon fibers, boron fibers, etc. Particulate reinforcements which may be utilized include glass or metal microspheres and flakes, talc, Wallastonite, chalk, clays, etc.

Since generally the elastic modulus or stiffness of a polymer increases with increasing amounts of reinforcement fillers, the elastic modulus of each discrete layer of the composite polymer layer such as is shown in FIG. 5, may be varied by varying the amount of filler, of the same type, in each layer. However, if desired, the type of filler in each layer may be varied. Similarly, amounts and types of filler in each layer may be varied in combination with, if desired, either a constant or varying amount of plasticizer in each layer.

Moreover, the modulus of elasticity of each layer can be varied by varying the chemical constituents of each layer. Thus, the most interior layer, layer 32a, may be composed of a relatively hard polymer such as polymethylmethacrylate or a melamine-formaldehyde resin. Layer 32b may be composed of a softer polymer or copolymer such as polymethylmethacrylate having been modified by a softer copolymer such as, for example, polybutylacrylate. Layer 32c will be composed of an even more elastic polymer or copolymer, and finally, layer 32d will be composed of the most elastic polymer or copolymer. Similarly, a very effective method of increasing polymer rigidity is by cross-linking. Thus, the innermost layer can be fully cross-linked with intermediate layers having varying amounts of cross-linking, and the exterior layer having no cross-linking.

FIG. 6 diagrammatically illustrates a fragmentary cross-section of an implant comprising a reinforcement element carrying a multi-layer polymer layer as in FIGS. 4 and 5 which has been fixedly attached to bone by means of bone cement, beneath which there is illustrated a graph of the elastic modulus of the different components of the reinforcement element/multi-layer polymer layer/bone cement/bone composite. Thus, reinforcement element 31 is shown to have a constant, high modulus of elasticity represented by line 34. The polymer layer is shown to be composed of four layers 32a, 32b, 32c and 32d, each having an incrementally lower but substantially constant modulus of elasticity as shown by lines 36a, 36b, 36c and 36d. Hardened bone cement 16 is shown to have a constant but lower modulus of elasticity represented by line 24. It can be seen that the outermost layer of the polymer layer, layer 32d, has a modulus of elasticity approximately equal to the modulus of elasticity of the bone cement while the innermost layer of the polymer layer 32a, has the highest modulus of elasticity which is approximately equal to the modulus of elasticity of the reinforcement element.

Formation of the multi-layered polymer layer on the reinforcement element may be accomplished by any suitable means, such as by dipping or the utilization of by a series of molds after treatment of the reinforcement element to insure proper adhesion of the polymer layer. Such treatment of the reinforcement element may comprise removal of weak boundary layers as described in applicant's previously referred-to copending application, Ser. No. 45,657, filed June 5, 1979, which is hereby incorporated by reference.

Where the reinforcement element has a relatively simple shape, such as the reinforcement element shown in FIG. 4, formation of the multi-layered polymer layer may be accomplished by dipping. Thus, there may be provided, for example, four containers containing a molten polymer, such as polymethylmethacrylate. The molten polymer in the first container has no plasticizer. The molten polymer in the second container includes a small amount of plasticizer. The molten polymer in the third container includes a greater amount of plasticizer, while the molten polymer in the fourth and final container contains the greatest amount of plasticizer. A reinforcement element is dipped into the molten polymer in the first container and removed. After the polymer has hardened on the reinforcement element, it is again dipped into the first container. The is continued until there is a layer having a thickness of approximately 0.125 cm. Thereafter, the reinforcement element which now has the first discrete polymer layer thereon is dipped into the second container. This is continued as with dipping in the first container until the second layer has a thickness of about 0.125 cm.; thus, the composite polymer layer now has a thickness of 0.250 cm. In a like manner, the reinforcement element having the two-layer polymer layer is dipped in the third container until a layer of approximately 0.125 cm. is formed. Thus, the polymer composite layer now has a thickness of about 0.375 cm. Finally, the reinforcement element having the polymer layer thereon is dipped in the fourth container until the composite polymer layer has a total thickness of 0.50 cm.

The composite polymer layer may be composed of more or less than four discrete polymer layers, and, as shown in FIG. 5, it is not necessary that each discrete polymer layer have the same thickness. In fact, it may be desired in some instances that no layer have the same thickness.

Another method of forming the multi-layered polymer layer disposed upon the reinforcement element comprises the utilization of a series of molds. Thus, there can be provided a series of progressively larger molds. The reinforcement element is placed in the first mold and a polymer is likewise placed into the first mold to provide a first layer of polymer material having a relatively high modulus of elasticity, preferably closely approximating that of the reinforcement element. The reinforcement element having one polymer layer thereon is thereafter placed into the second mold, which is larger than the first mold and a polymer material having a lower modulus of elasticity when hardened due to, e.g., the inclusion of a greater amount of plasticizer or a smaller amount of filler, is provided in the second mold. The polymer material which may be either a thermoplastic or thermosetting resin is allowed to harden, thus providing a second layer of polymer material. Thereafter, the reinforcing element having two layers of polymer material thereon is treated in a third, larger mold, and the process may be continued using progressively larger molds containing progressively less rigid polymer material, until the desired degree of thickness and flexibility is obtained.

Figure 7:
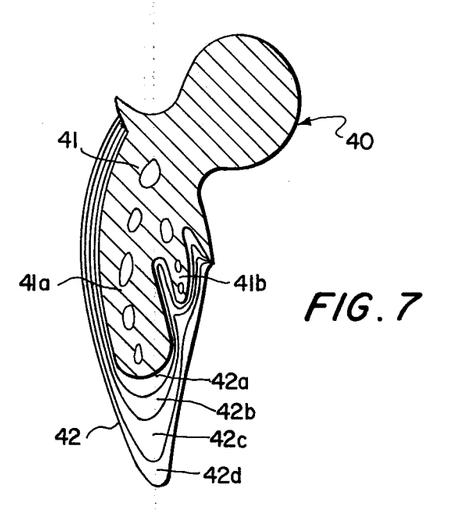
FIG. 7 is a side elevational view in longitudinal section of a polymer encapsulated hip prosthesis prepared in accordance with another aspect of the present invention.

According to another aspect of the present invention, the use of a polymer layer or capsule allows for a complex reinforcement element shape in the provision of e.g., a bone insert prosthesis, while the external surface of the insert, i.e., the bone attachment surface, can have a simple shape. FIG. 7 illustrates such a prosthesis wherein the reinforcement element has a complex, physiologically designed reinforcement structure whereby the force distribution throughout the prosthesis may be more properly controlled, while the external polymer layer covering the complexly shaped surface provides a simple, nearly frustoconical external surface, suitable for insertion into a bone cavity. Thus, FIG. 7 is a side elevational view in longitudinal section of a polymer encapsulated hip prosthesis 40. Reinforcement element 41, which is composed of a highly rigid material such as a metal alloy or UHMWPE, is shown to have a main finger-like portion 41a and a smaller finger-like appendage 41b. The provision of the multiple appendages 41a and 41b can accomplish a more even force distribution. However, due to the irregular shape of the reinforcement element, it cannot be suitably inserted into a bone cavity containing bone cement. By encapsulating the irregular reinforcement element 41 with polymer layer 42, the insert may be provided with a regular shape as shown in FIG. 7. Thus, irregularly shaped reinforcement elements, i.e., having multiple concave and convex portions, may be designed and may thereafter be encapsulated or covered by a polymer layer so that the entire composite has a simple, regular shape. By the term "regular", it is meant a generally smooth, three-dimensional surface having no significant concave or convex portions other than the overall, e.g., frustoconical, shape.

It will be noted that the polymer layer 42 shown in FIG. 7 is composed of four layers 42a, 42b, 42c and 42d. Thus, the polymer layer is designed so as to have a varying modulus of elasticity as hereinbefore described. If desired, the polymer layer may be a single, continuous layer wherein the modulus of elasticity is varied by means of, e.g., a varying void volume as hereinbefore discussed.

Formation of prosthetic elements wherein the reinforcement element has an irregular, complex shape which complex shape is covered by a polymer layer, the external surface of which has a regular, simple shape, may be accomplished by any suitable means, particularly the means hereinbefore described. It should be noted that where a multi-layered, composite polymer layer is desired, the use of the dipping technique herein described will normally not be suitable.

Figure 8:
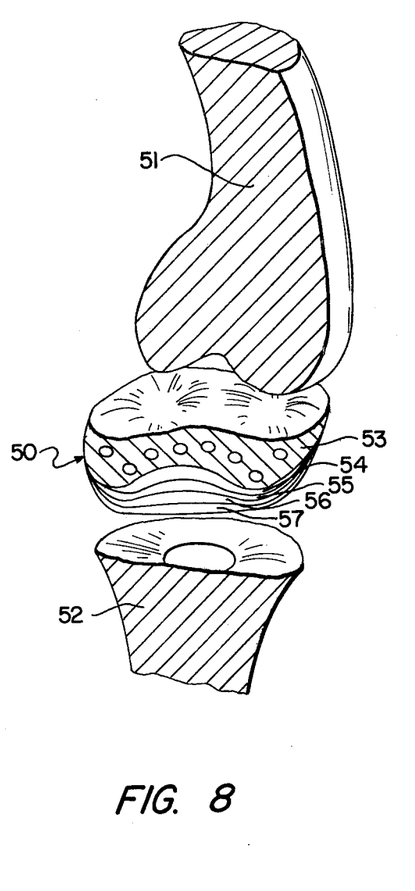
FIG. 8 is an exploded perspective view in vertical section of a human knee joint wherein the tibial component of the knee joint has been replaced by a prosthesis prepared in accordance with the present invention.

FIG. 8 is an exploded perspective view in vertical section of a human knee joint wherein the tibial component of the knee joint has been replaced by a prosthesis prepared in accordance with the present invention. Thus, a vertical section of the femur component of the knee joint is shown at 51. Tibia 52 has been treated so as to remove the damaged knee joint component. The prosthetic element 50 which is to be joined to the damaged tibia, is composed of rigid reinforcement element 53 and a composite polymer layer composed of four discrete layers 54, 55, 56 and 57. Reinforcement element 53 is composed of a rigid material such as a metal alloy or UHMWPE. The reinforcement element is shown as having a complex shape including two depressions for receiving the condyles of the femur and two corresponding convex protrusions or bulges on the opposite side of the reinforcement element. While such a complex shape provides for an even force distribution across the prosthesis, great difficulties would be encountered in joining such a complex shape to bone. Thus, a composite polymer layer comprising discrete polymer layers 54, 55, 56 and 57, and together which form a regular convex surface, are provided as the bone attachment surface. As previously described, the polymer layers are designed so that the composite polymer layer has a varying modulus of elasticity. Thus, polymer layer 54 has the greatest modulus of elasticity while polymer layer 57 has the least modulus of elasticity. Polymer layer 55 has a modulus of elasticity greater than that of polymer layer 56 but less than that of polymer layer 54. Polymer layer 56 has a modulus of elasticity greater than that of polymer layer 57 but less than that of polymer layer 54. If desired, a continuous polymer layer having a varying modulus of elasticity may be substituted for the composite polymer layer shown in FIG. 8.

Other resurfacing implants may be designed in accordance with the present invention. Thus, for instance, an acetabalum or hip joint socket implant may be designed in accordance with the teachings hereinbefore set forth. A hemispherical or cup-shaped prosthetic element having a concave surface designed to receive a femur head is provided. The element is composed of a rigid alloy such as ZIMALOY or plastic such as UHMWPE. The convex surface of the implant, designed to be attached to bone, includes a polymer layer having a varying modulus of elasticity as previously described. The convex surface of the rigid reinforcement element may be a simple, regular hemisphere or it may have a complex shape, including protrusions and concave surfaces designed in accordance with engineering principles so as to provide an even force distribution throughout the implant. Such convex surface, either regular or complex, of the reinforcement element will be covered with a polymer layer having a varying modulus of elasticity, which layer constitutes the bone attachment surface. The polymer layer may be a continuous layer or a composite layer as hereinbefore shown.

I claim:

1. A prosthesis adapted to be fixedly attached to bone by means of bone cement, said prosthesis comprising a reinforcement element, at least a portion of the surface of said reinforcement element carrying a polymer layer having substantial thickness, the exterior surface of said polymer layer constituting the bone attachment surface of said prosthesis, the interior surface of said polymer layer being secured to said reinforcement element, said polymer layer having a varying modulus of elasticity such that the modulus of elasticity of portions of said layer adjacent said interior surface is essentially constant and the modulus of elasticity of portions adjacent said exterior surface is essentially constant, said modulus of elasticity of said portions adjacent said interior surface being greater than said modullus of elasticity of said portions adjacent said exterior surface, portions of said layer which are between said portions adjacent said exterior surface and said portions adjacent said interior surface having a modulus of elasticity which is intermediate with respect to the moduli of said portions adjacent said exterior and interior surfaces and wherein the modulus of elasticity of said layer decreases in the direction of interior to exterior.

2. A prosthesis in accordance with claim 1 wherein the modulus of elasticity of said portions of said layer adjacent said exterior surface is approximately equal to the modulus of elasticity of hardened bone cement.

3. A prosthesis in accordance with claim 2 wherein the modulus of elasticity of said portions of said layer adjacent said interior surface is approximately equal to the modulus of elasticity of said reinforcement element.

4. A prosthesis in accordance with claim 1 wherein said modulus of elasticity of said layer decreases continuously in the direction of interior to exterior.

5. A prosthesis in accordance with claim 4 wherein said polymer layer comprises voids, said voids being distributed throughout said polymer layer such that the percentage of volume occupied by voids in portions of said layer adjacent said exterior surface is greater than the percentage of volume occupied by voids in portions of said layer adjacent said interior surface, said void volume percentage continuously increasing in the direction of interior to exterior of said layer.

6. A prosthesis in accordance with claim 5 wherein the percentage of volume occupied by voids in said portions of said layer adjacent said interior surface is about zero.

7. A prosthesis in accordance with claim 5 wherein said reinforcement element consists essentially of metal.

8. A prosthesis in accordance with claim 7 wherein said polymer layer has a thickness of greater tha 0.10 cm.

9. A prosthesis in accordance with claim 8 wherein said prosthesis is a stem insertion prosthesis.

10. A prosthesis in accordance with claim 1 wherein said modulus of elasticity of said polymer layer decreases incrementally in the direction of interior to exterior.

11. A prosthesis in accordance with claim 10 wherein said polymer layer is a composite of discrete polymer layers each having a different modulus of elasticity.

12. A prosthesis in accordance with claim 11 wherein each of said discrete polymer layers comprises a different amount of a plasticizer.

13. A prosthesis in accordance with claim 12 wherein each of said layers has a greater amount of plasticizer than the adjacent, more interior layer.

14. A prosthesis in accordance with claim 11 wherein each of said discrete layers comprises a different amount of a reinforcement filler.

15. A prosthesis in accordance with claim 14 wherein said reinforcement filler is a particulate material.

16. A prosthesis in accordance with claim 14 wherein said reinforcement filler is a fiberous material.

17. A prosthesis in accordance with claim 14 wherein each of said layers has a lesser amount of reinforcement filler than the adjacent, more interior layer.

18. A prosthesis in accordance with claim 1 wherein said reinforcement element has an irregular shape and wherein the external surface of said polymer layer has a simple, regular shape.

19. A prosthesis in accordance with claim 18 wherein said reinforcement element is composed of a metal.

20. A prosthesis in accordance with claim 18 wherein said prosthesis is a stem insertion prosthesis.

21. A prosthesis in accordance with claim 19 wherein said prosthesis is a stem insertion prosthesis.

* * * * *